United States Patent
Wang et al.

(10) Patent No.: US 11,986,307 B2
(45) Date of Patent: May 21, 2024

(54) DIGITAL SIGNAL PROCESSING ASSISTANT MODELING METHOD FOR BIOSIGNAL ANALYSIS

(71) Applicant: TENCENT AMERICA LLC, Palo Alto, CA (US)

(72) Inventors: Kun Wang, San Jose, CA (US);
Xiaozhong Chen, Cedarburg, WI (US);
Xu Wang, Palo Alto, CA (US);
Shangqing Zhang, San Jose, CA (US);
Min Tu, Cupertino, CA (US); Wei Fan, New York, NY (US)

(73) Assignee: TENCENT AMERICA LLC, Palo Alto, CA (US)

( * ) Notice: Subject to any disclaimer, the term of this patent is extended or adjusted under 35 U.S.C. 154(b) by 410 days.

(21) Appl. No.: 16/562,576

(22) Filed: Sep. 6, 2019

(65) Prior Publication Data
US 2021/0068691 A1    Mar. 11, 2021

(51) Int. Cl.
| | |
|---|---|
| *A61B 5/316* | (2021.01) |
| *A61B 5/00* | (2006.01) |
| *A61B 5/0533* | (2021.01) |
| *A61B 5/245* | (2021.01) |
| *A61B 5/318* | (2021.01) |
| *A61B 5/369* | (2021.01) |
| *A61B 5/389* | (2021.01) |
| *A61B 5/398* | (2021.01) |
| *G16H 50/20* | (2018.01) |
| *G06N 3/04* | (2023.01) |
| *G06N 3/044* | (2023.01) |
| *G06N 20/10* | (2019.01) |

(52) U.S. Cl.
CPC ............ *A61B 5/316* (2021.01); *A61B 5/0533* (2013.01); *A61B 5/245* (2021.01); *A61B 5/318* (2021.01); *A61B 5/369* (2021.01); *A61B 5/389* (2021.01); *A61B 5/398* (2021.01); *A61B 5/7257* (2013.01); *A61B 5/726* (2013.01); *A61B 5/7264* (2013.01); *A61B 5/7275* (2013.01); *A61B 5/746* (2013.01); *G16H 50/20* (2018.01); *G06N 3/04* (2013.01); *G06N 3/044* (2023.01); *G06N 20/10* (2019.01)

(58) Field of Classification Search
CPC ......... A61B 5/316; A61B 5/725; A61B 5/726; A61B 5/7264; A61B 5/746
See application file for complete search history.

(56) References Cited

U.S. PATENT DOCUMENTS

2017/0032221 A1    2/2017  Wu et al.
2018/0106897 A1    4/2018  Shouldice et al.

OTHER PUBLICATIONS

International Search Report in International Application No. PCT/US20/45891 dated Nov. 23, 2020.
Written Opinion of the International Searching Authority of PCT/US20/45891 dated Nov. 23, 2020.

*Primary Examiner* — James M Kish
*Assistant Examiner* — Jessica L Mullins
(74) *Attorney, Agent, or Firm* — Sughrue Mion, PLLC

(57) ABSTRACT

A method and apparatus for performing a biosignal analysis task using a set of models includes receiving an input biosignal. Information that identifies the biosignal analysis task to be performed in association with the input biosignal is received. A waveform model and a digital signal processing (DSP) model are selected. A first type of feature and a second type of feature of the input biosignal are identified. An analysis model is selected, and the biosignal analysis task is performed using the analysis model.

8 Claims, 4 Drawing Sheets

DIGITAL SIGNAL PROCESSING ASSISTANT MODELING METHOD FOR BIOSIGNAL ANALYSIS

BACKGROUND

An electrocardiogram (ECG) signal is one of the most common waveform biosignals which can help doctors diagnose many heart diseases, including atrial fibrillation, myocardial infarction, and acute coronary syndrome (ACS). Annually, around 300 million ECGs are recorded. Conventional approaches for ECG analysis tend to use digital signal processing algorithms, such as wavelet transformations, to compute features from ECG signals.

However, such approaches are not comprehensive and, thus, using them alone is often times insufficient for distinguishing multiple types of heart arrhythmias. Recent approaches have adopted deep neural networks, such as convolutional neural networks (CNNs) and recurrent neural networks (RNNs), and provide improved accuracy for multi-class classification tasks based on ECG signals.

SUMMARY

According to some possible implementations, a method for performing a biosignal analysis task using a set of models includes receiving an input biosignal; receiving information that identifies the biosignal analysis task to be performed in association with the input biosignal; selecting a waveform model, from a set of waveform models, to be used to identify a first type of feature of the input biosignal, based on the information that identifies the biosignal analysis task to be performed; selecting a digital signal processing (DSP) model, from a set of DSP models, to be used to identify a second type of feature of the input biosignal, based on the information that identifies the biosignal analysis task to be performed; identifying, using the waveform model, the first type of feature of the input biosignal; identifying, using the DSP model, the second type of feature of the input biosignal; selecting an analysis model, from a set of analysis models, to perform the biosignal analysis task associated with the input biosignal, based on the first type of feature and the second type of feature; and performing, using the analysis model, the biosignal analysis task based on the first type of feature and the second type of feature.

According to some possible implementations, a device for performing a biosignal analysis task using a set of models comprises at least one memory configured to store program code; and at least one processor configured to read the program code and operate as instructed by the program code, the program code including: receiving code configured to cause the at least one processor to receive an input biosignal, and receive information that identifies the biosignal analysis task to be performed in association with the input biosignal; first selecting code configured to cause the at least one processor to select a waveform model, from a set of waveform models, to be used to identify a first type of feature of the input biosignal, based on the information that identifies the biosignal analysis task to be performed, and select a digital signal processing (DSP) model, from a set of DSP models, to be used to identify a second type of feature of the input biosignal, based on the information that identifies the biosignal analysis task to be performed; identifying code configured to cause the at least one processor identify, using the waveform model, the first type of feature of the input biosignal, and identify, using the DSP model, the second type of feature of the input biosignal; second selecting code configured to cause the at least one processor to select an analysis model, from a set of analysis models, to perform the biosignal analysis task associated with the input biosignal, based on the first type of feature and the second type of feature; and performing code configured to cause the at least one processor to perform, using the analysis model, the biosignal analysis task based on the first type of feature and the second type of feature According to some possible implementations, a non-transitory computer-readable medium stores instructions, the instructions comprising: one or more instructions that, when executed by one or more processors of a device, cause the one or more processors to: receive an input biosignal; receive information that identifies the biosignal analysis task to be performed in association with the input biosignal; select a waveform model, from a set of waveform models, to be used to identify a first type of feature of the input biosignal, based on the information that identifies the biosignal analysis task to be performed; select a digital signal processing (DSP) model, from a set of DSP models, to be used to identify a second type of feature of the input biosignal, based on the information that identifies the biosignal analysis task to be performed; identify, using the waveform model, the first type of feature of the input biosignal; identify, using the DSP model, the second type of feature of the input biosignal; select an analysis model, from a set of analysis models, to perform the biosignal analysis task associated with the input biosignal, based on the first type of feature and the second type of feature; and perform, using the analysis model, the biosignal analysis task based on the first type of feature and the second type of feature.

DETAILED DESCRIPTION

Figure 1:
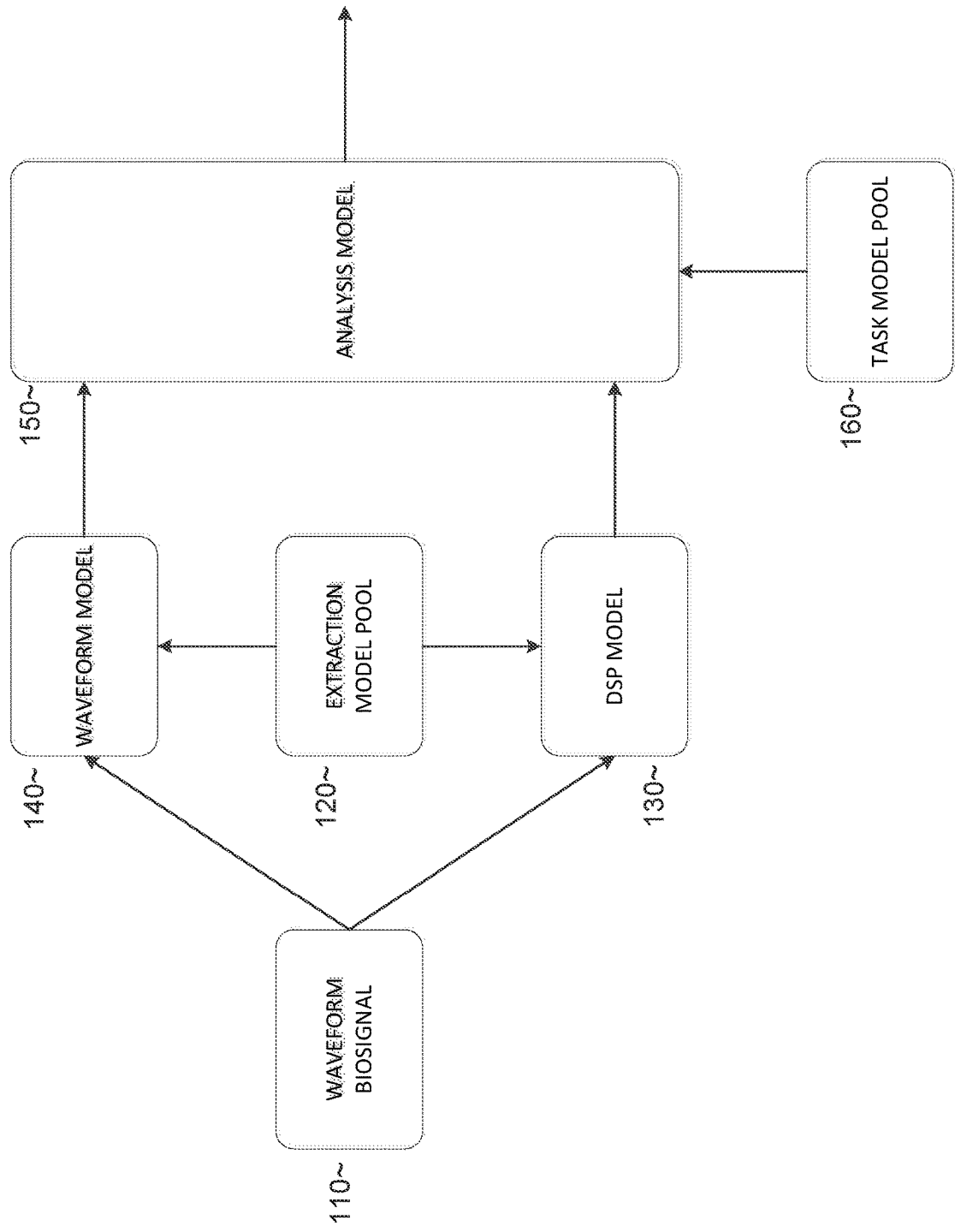
FIG. 1 is a diagram of an overview of an example implementation described herein.

The digital signal processing (DSP) assistant modeling method of the present disclosure is configured for waveform biosignal analysis. A biosignal is any signal produced by a living being that can be continually measured and monitored. For instance, a biosignal may be measured via electrocardiogram (ECG), electroencephalogram (EEG), electromyogram (EMG), mechanomyogram (MMG), electrooculography (EOG), galvanic skin response (GSR), and magnetoencephalogram (MEG).

By way of the present disclosure, doctors, researchers and other healthcare practitioners can apply artificial intelligence (AI) algorithms in symptom and disease classification, computer-aided diagnosis, bed-side alarm, and patient monitoring. A waveform biosignal that is used for the modeling procedure can be from a single source or multiple sources. For instance, a standard ambulatory ECG report contains signals from twelve leads which requires ten electrodes in contact with the body. When performing diagnosis using ECG signals, two levels of signal patterns might be considered by cardiologists and doctors. The first is an intra-heartbeat pattern which captures the signal changes with single heartbeats. The second is an inter-heartbeat pattern which measures shape alternations among multiple heartbeats.

Different types of conventional DSP algorithms have been applied to ECG diagnosis for decades. These algorithms provide understandable statistical/mathematical features, but require domain knowledge and expensive and time consuming DSP and feature engineering procedures. The present disclosure provides an artificial intelligence framework for ECG analysis, which accepts both ECG signals and raw DSP features as inputs and provides possible analysis outcomes as well as the reasons of decision. For instance, comprehensive multi-lead ECG signals and corresponding DSP results can be used, and the final results of the framework can be the diagnosis (e.g., atrial premature complexes) and suspect heartbeat (e.g., $3^{rd}$, $6^{th}$, etc). Specifically, the present disclosure provides a DSP feature extraction module, a waveform feature extraction module and a comprehensive task-specific analysis module according to an embodiment.

Although the existing approaches for cardiologic tasks have provided promising results in terms of accuracy, there are still several challenges and shortages. For instance, machine learning and deep learning provide performance advantages, however, they lack the ability of helping doctors and patients understand the reasons for diagnosis. The researcher, as well as the cardiologists, might not be able to directly utilize the models to explain where, how, or why the model makes a final decision.

The DSP features have thousands of alternatives, and finding the balance point between model complexity and performance is an exhausting procedure. Complex models can provide better performance results theoretically since such models are able to capture more variance in the feature space. However, complex models also might require additional computation time and introduce computational complexity.

In short, according to some approaches, cardiologists might not be able to fully utilize models in practice, and cannot make comprehensive decisions based on their complexity.

The present disclosure permits multiple data analysis tasks with multiple types of features. Features may be extracted with different feature extraction modules. According to an embodiment, the first type of feature may be a waveform feature embedded in the sequence of digital reading of biosignals. These features may help identify symptoms and diseases related to signal changes, for instance, T wave inversion, premature beats, sinus rhythm, etc.

According to an embodiment, the second type are DSP features which may be acquired by different types of signal processing algorithms, for instance, fast Fourier transform, wavelet transform, filters, etc. Both types of extracted features are collected for the final analysis module. Therefore, the proposed analysis framework can be widely applied to various types of analysis tasks.

As mentioned, the framework of the present disclosure includes two major modules: 1) a set of feature extraction modules (e.g., waveform and DSP) which analyze input information and extract high-level data features. Attention mechanisms are alternative for each extraction module to model hidden relationships and data-result dependency; and 2) an analysis module which finishes a specific task such as clustering, classification, prediction, etc., and then provides the final goal of the framework.

Referring to FIG. 1, the feature extraction modules receive pre-processed data as inputs, and generate feature vectors as outputs. For example, as shown, a waveform biosignal 110 is provided to a models from an extraction model pool 120. Specifically, the waveform biosignal 110 is provided to a DSP model 130 and a waveform model 140. Model-wise, the extraction modules may be: 1) signal processing algorithms such as filtering, fast Fourier transform, and wavelet transform for DSP features; and 2) machine learning approaches such as support vector machines (SVMs), random forests (RFs), or deep learning models such as CNNs and RNNs.

The parameters for each module may be trained and/or selected separately. According to an embodiment, an attention mechanism can be alternatively attached to each module to model the dependency and relationships between input and output, and among outputs. For instance, if an ECG signal was diagnosed as an atrial premature complex, there may be a strong likelihood that the same signal would not be diagnosed as a sinus rhythm at the same time; if a signal exhibits an unchanged pattern among all heartbeats, it has a high probability to be diagnosed as a normal ECG as well as sinus rhythm. Such dependencies can be modeled as an RNN model, Bayesian network, etc. that provide decisions based on both input and output information.

According to an embodiment, the extracted features are collected from multiple modules with multiple types of inputs. These features are post-processed, for instance, using batch normalization, instance normalization, etc. to provide a final feature set for analysis.

As shown in FIG. 1, an analysis model 150 is selected from a task model pool 160. The final module in the present disclosure is a biosignal analysis module which receives extracted features, and produces final outcomes such as classification results, outlier alarms, predicted diagnosis, and/or the like. As shown in FIG. 1, the task specific module pool may be a collection of different models configured for various biosignal related tasks. For instance, the task specific module pool may include several statistical process control algorithms for biosignal monitoring and alarming, several predictive models and classifier models for computer-aided diagnosis, and some statistical tools for general pathological status calculation. Depending on the desired output, the analysis module may deploy an appropriate tool from the pool to finish the end-to-end framework and achieve the final goal.

The proposed training framework of the present disclosure is designed as an end-to-end framework. Compared to existing approaches of biosignal analysis models, the present disclosure can extract features from multiple perspectives simultaneously. More specifically, as shown, the present disclosure can extract waveform features and DSP features. In real-world diagnosis, a doctor should consider multi-perspective, heterogeneous, and even hierarchical structural features to render a comprehensive conclusion.

The present disclosure also merges features from multiple inputs in different forms. Another advantage is that the present disclosure assists researchers and doctors to better understand the correlation between biosignals and the analysis results, such as diagnosis. Moreover, the present disclosure is capable of being extended to other architectures by applying an optional dependence network based on existing cases as the attention add on for different extraction modules.

According to some embodiments, the extraction module may use a combination of several algorithms and structures, for instance, RNN with CNN, RNN with SVM, etc. Since the flexibility of definition of "feature" in machine learning, the exact implementation of extraction modules may vary.

The perspectives of feature extraction are flexible. According to an embodiment, waveform and DSP categories are used. As alternatives, statistical features such as moving average and autocorrelations for feature extraction are used. Moreover, the attention add ons are also flexible, meaning that they can be used or not used for certain modules, and the same or different attentions for different modules can be used, depending on the requirement and purpose of feature extraction.

According to an embodiment, and for feature extraction modules, similar models are configured to share a subset of parameters to account for similarity among inputs.

By the present disclosure, the framework is designed as an end-to-end procedure and the whole framework can be optimized and altered simultaneously. An alternative is a step-by-step training procedure, in which the extraction modules can be trained separately, for instance, using encoder and decoder structures.

This approach can be extended to other applications which have multiple sources of input. For instance, one model could use both ECG and EEG as sources, and extract features separately. The analysis model can either accept each feature set respectively or both sets comprehensively.

Based on the extraction modules and analysis tasks we select to apply with, optional feedback mechanisms can be added from output to feature extraction modules. For instance, we are using RNN model for multi-symptom diagnosis. To account for the dependency as mentioned among symptoms, a feedback link can be added from diagnosed symptoms to feature extraction, to tell the module how and where it should concentrate in the following steps.

Figure 2:
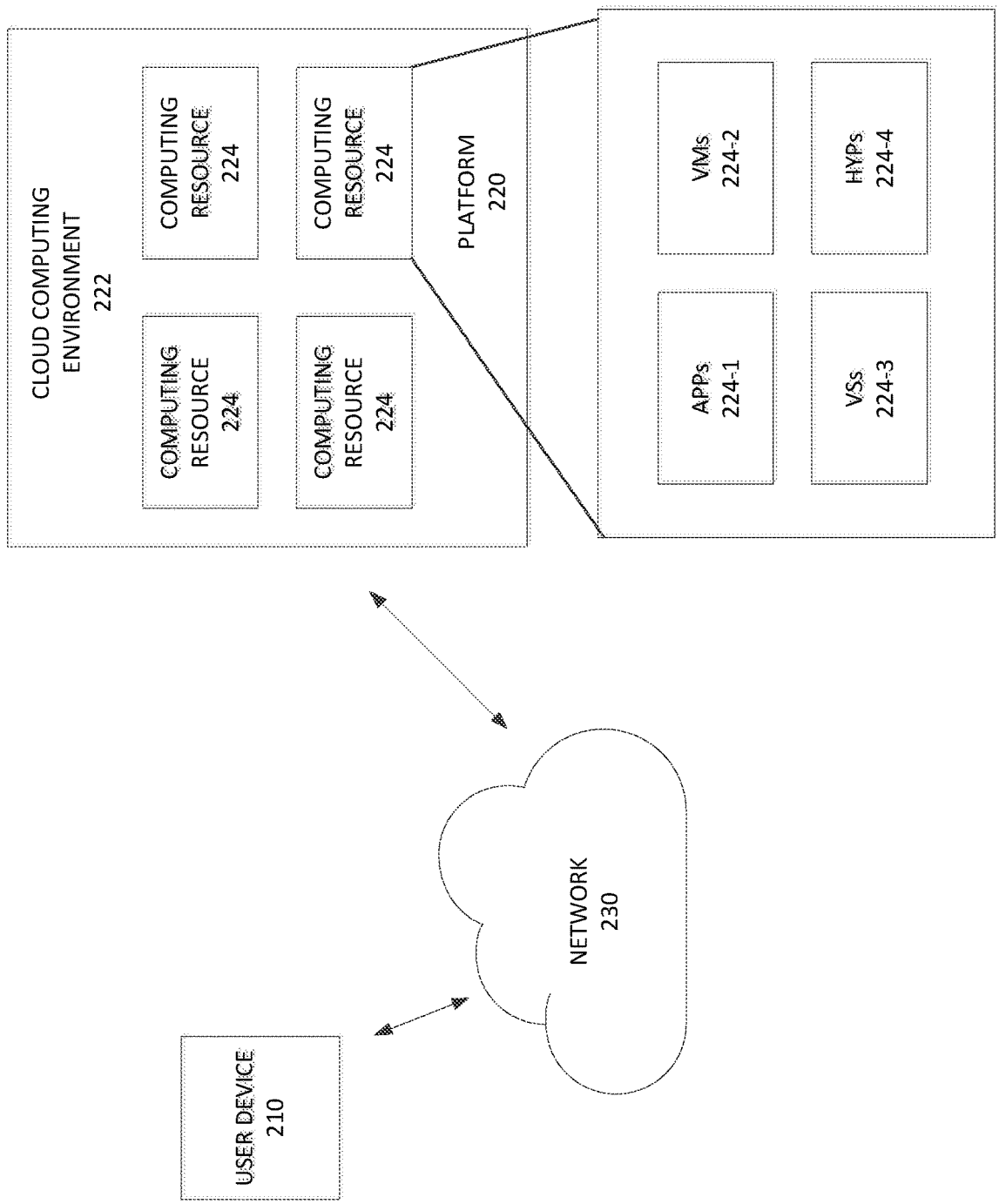
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a user device 210, a platform 220, and a network 230. Devices of environment 200 may interconnect via wired connections, wireless connections, or a combination of wired and wireless connections.

User device 210 includes one or more devices capable of receiving, generating, storing, processing, and/or providing information associated with platform 220. For example, user device 210 may include a computing device (e.g., a desktop computer, a laptop computer, a tablet computer, a handheld computer, a smart speaker, a server, etc.), a mobile phone (e.g., a smart phone, a radiotelephone, etc.), a wearable device (e.g., a pair of smart glasses or a smart watch), or a similar device. In some implementations, user device 210 may receive information from and/or transmit information to platform 220.

Platform 220 includes one or more devices capable of performing a biosignal analysis task using a set of models, as described elsewhere herein. In some implementations, platform 220 may include a cloud server or a group of cloud servers. In some implementations, platform 220 may be designed to be modular such that certain software components may be swapped in or out depending on a particular need. As such, platform 220 may be easily and/or quickly reconfigured for different uses.

In some implementations, as shown, platform 220 may be hosted in cloud computing environment 222. Notably, while implementations described herein describe platform 220 as being hosted in cloud computing environment 222, in some implementations, platform 220 is not be cloud-based (i.e., may be implemented outside of a cloud computing environment) or may be partially cloud-based.

Cloud computing environment 222 includes an environment that hosts platform 220. Cloud computing environment 222 may provide computation, software, data access, storage, etc. services that do not require end-user (e.g., user device 210) knowledge of a physical location and configuration of system(s) and/or device(s) that hosts platform 220. As shown, cloud computing environment 222 may include a group of computing resources 224 (referred to collectively as "computing resources 224" and individually as "computing resource 224").

Computing resource 224 includes one or more personal computers, workstation computers, server devices, or other types of computation and/or communication devices. In some implementations, computing resource 224 may host platform 220. The cloud resources may include compute instances executing in computing resource 224, storage devices provided in computing resource 224, data transfer devices provided by computing resource 224, etc. In some implementations, computing resource 224 may communicate with other computing resources 224 via wired connections, wireless connections, or a combination of wired and wireless connections.

As further shown in FIG. 2, computing resource 224 includes a group of cloud resources, such as one or more applications ("APPs") 224-1, one or more virtual machines ("VMs") 224-2, virtualized storage ("VSs") 224-3, one or more hypervisors ("HYPs") 224-4, or the like.

Application 224-1 includes one or more software applications that may be provided to or accessed by user device 210 and/or sensor device 220. Application 224-1 may eliminate a need to install and execute the software applications on user device 210. For example, application 224-1 may include software associated with platform 220 and/or any other software capable of being provided via cloud computing environment 222. In some implementations, one application 224-1 may send/receive information to/from one or more other applications 224-1, via virtual machine 224-2.

Virtual machine 224-2 includes a software implementation of a machine (e.g., a computer) that executes programs like a physical machine. Virtual machine 224-2 may be either a system virtual machine or a process virtual machine, depending upon use and degree of correspondence to any real machine by virtual machine 224-2. A system virtual machine may provide a complete system platform that supports execution of a complete operating system ("OS"). A process virtual machine may execute a single program, and may support a single process. In some implementations, virtual machine 224-2 may execute on behalf of a user (e.g., user device 210), and may manage infrastructure of cloud computing environment 222, such as data management, synchronization, or long-duration data transfers.

Virtualized storage 224-3 includes one or more storage systems and/or one or more devices that use virtualization techniques within the storage systems or devices of computing resource 224. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored.

This may enable optimization of storage use, server consolidation, and/or performance of non-disruptive file migrations.

Hypervisor 224-4 may provide hardware virtualization techniques that allow multiple operating systems (e.g., "guest operating systems") to execute concurrently on a host computer, such as computing resource 224. Hypervisor 224-4 may present a virtual operating platform to the guest operating systems, and may manage the execution of the guest operating systems. Multiple instances of a variety of operating systems may share virtualized hardware resources.

Network 230 includes one or more wired and/or wireless networks. For example, network 230 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
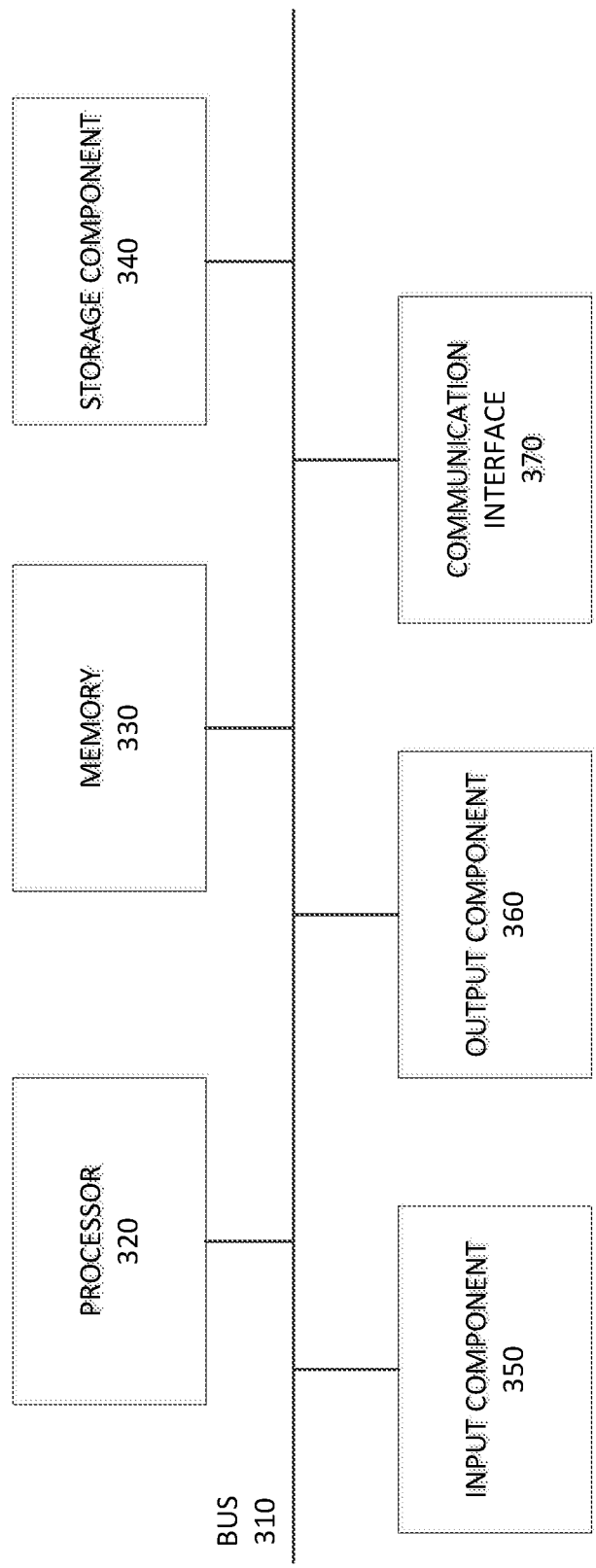
FIG. 3 is a diagram of example components of one or more devices of FIG. 2.

FIG. 3 is a diagram of example components of a device 300. Device 300 may correspond to user device 210 and/or platform 220. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
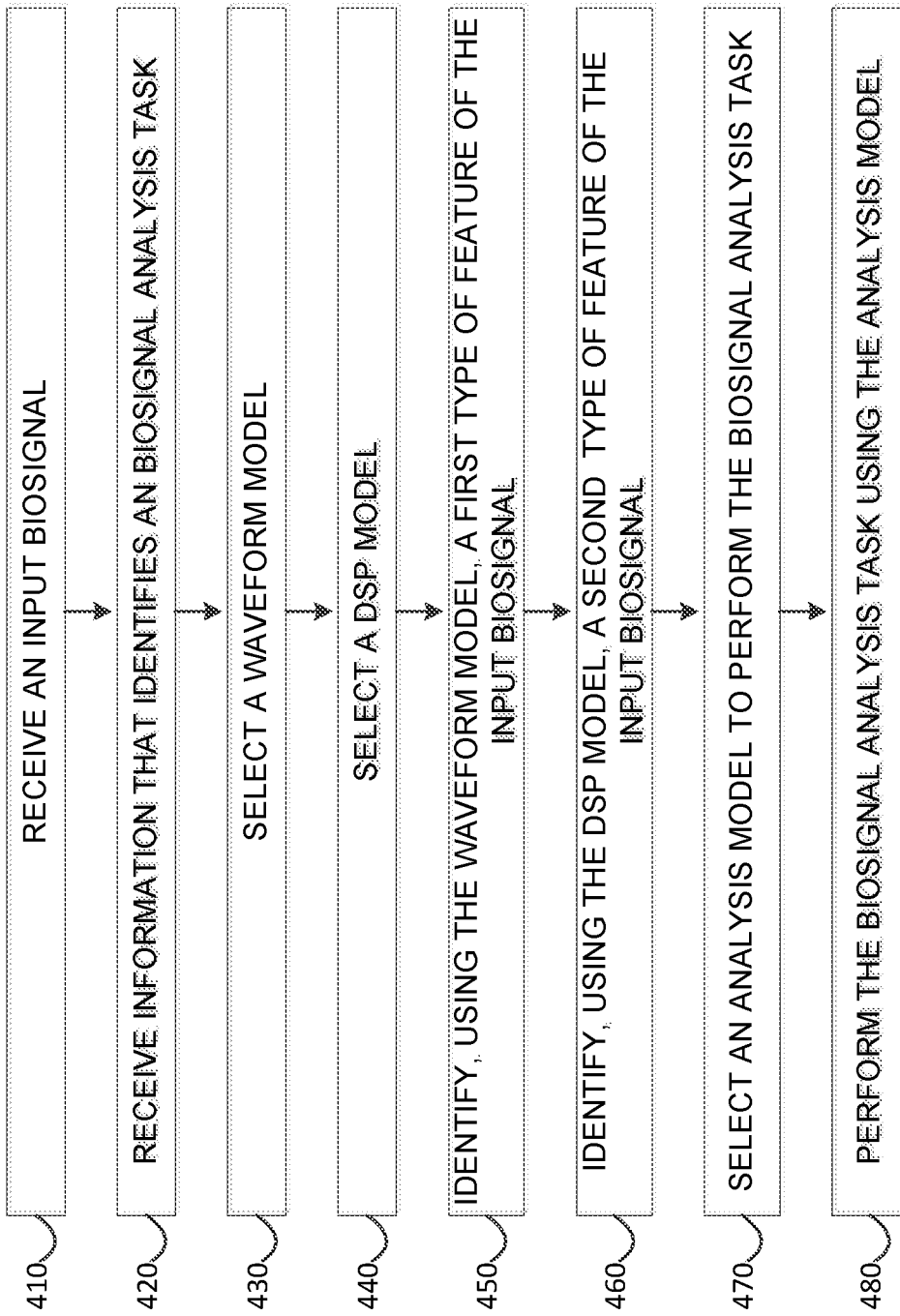
FIG. 4 is a flow chart of an example process for performing a biosignal analysis task using a set of models.

FIG. 4 is a flow chart of an example process 400 for performing a biosignal analysis task using a set of models. In some implementations, one or more process blocks of FIG. 4 may be performed by platform 220. In some implementations, one or more process blocks of FIG. 4 may be performed by another device or a group of devices separate from or including platform 220, such as user device 210.

As shown in FIG. 4, process 400 may include receiving an input biosignal (block 410). For example, platform 220 may receive an input biosignal from another device, from a storage, and/or the like.

The input biosignal may be an electrocardiogram (ECG) signal, an electroencephalogram (EEG) signal, an electromyogram (EMG) signal, a mechanomyogram (MMG) signal, an electrooculography (EOG) signal, a galvanic skin response (GSR) signal, an magnetoencephalogram (MEG) signal, and/or the like.

In some implementations, platform 220 may receive a single type of biosignal, and perform the operations of FIG. 4. Alternatively, platform 220 may receive multiple types of biosignals (e.g., an ECG signal and an EEG signal, etc.) and perform the operation of the FIG. 4.

As further shown in FIG. 4, process 400 may include receiving information that identifies the biosignal analysis task to be performed in association with the input biosignal (block 420). For example, platform 220 may receive information that identifies a particular type of biosignal task to be performed using the input biosignal. Platform 220 may receive the information from another device, from a storage, and/or the like.

The biosignal analysis task may includes determining a diagnosis of a condition associated with the input biosignal, clustering the input biosignal, classifying the input biosignal, predicting a disease associated with the input biosignal, biosignal monitoring, biosignal alarming, patient monitoring, and/or the like.

As further shown in FIG. 4, process 400 may include selecting a waveform model, from a set of waveform models, to be used to identify a first type of feature of the input biosignal, based on the information that identifies the biosignal analysis task to be performed (block 430).

In some implementations, platform 220 may access a pool of waveform models. For example, the pool of waveform models may refer to a set of models that may be used to perform waveform analysis of a biosignal. In this case, platform 220 may select a particular waveform model, from among the pool of waveform models, in order to identify a first type of feature of the input biosignal.

The first type of feature may include any type of feature of the input biosignal that is capable of being monitored, analyzed, and/or the like. As an example, the first type of feature may correspond to a waveform of the input biosignal, an amplitude of the input biosignal, a frequency of the input biosignal, and/or the like.

Platform 220 may identify the waveform model based on the selected biosignal analysis task. That is, platform 220 may store, in a data structure, information that maps waveform models and biosignal analysis tasks. In other words, platform 220 may identify, based on the selected biosignal analysis task, the particular waveform model to be used to perform the biosignal analysis task.

As further shown in FIG. 4, process 400 may include selecting a digital signal processing (DSP) model, from a set of DSP models, to be used to identify a second type of feature of the input biosignal, based on the information that identifies the biosignal analysis task to be performed (block 440).

In some implementations, platform 220 may access a pool of DSP models. For example, the pool of DSP models may refer to a set of models that may be used to perform DSP analysis of a biosignal. In this case, platform 220 may select a particular DSP model, from among the pool of DSP models, in order to identify a second type of feature of the input biosignal.

The second type of feature may include any type of feature of the input biosignal that is capable of being monitored, analyzed, and/or the like. As an example, the first type of feature may correspond to a waveform of the input biosignal, an amplitude of the input biosignal, a frequency of the input biosignal, and/or the like.

Platform 220 may identify the DSP model based on the selected biosignal analysis task. That is, platform 220 may store, in a data structure, information that maps DSP models and biosignal analysis tasks. In other words, platform 220 may identify, based on the selected biosignal analysis task, the particular DSP model to be used to perform the biosignal analysis task.

Additionally, or alternatively, platform 220 may store a data structure that maps waveform models and DSP models that are used to perform a particular biosignal analysis task. In this way, platform 220 may identify a waveform model and a DSP model to be used to perform the selected biosignal analysis task.

As further shown in FIG. 4, process 400 may include identifying, using the waveform model, the first type of feature of the input biosignal (block 450).

For example, platform 220 may input the input biosignal into the waveform model, and may identify the first type of feature based on an output of the waveform model. In some implementations, the waveform model may include a recurrent neural network (RNN), a convolutional neural network (CNN), a support vector machine (SVM), and/or the like. The waveform model may analyze an input biosignal, and generate an output that corresponds to the first type of feature of the input biosignal.

As further shown in FIG. 4, process 400 may include identifying, using the DSP model, the second type of feature of the input biosignal (block 460).

For example, platform 220 may input the input biosignal into the DSP model, and may identify the second type of feature based on an output of the DSP model. The DSP model may be configured to perform a filtering technique, a fast Fourier transform technique, a wavelet transform technique, and/or the like. The DSP model may analyze an input biosignal, and generate an output that corresponds to the second type of feature of the input biosignal.

As further show in FIG. 4, process 400 may include selecting an analysis model, from a set of analysis models, to perform the biosignal analysis task associated with the input biosignal, based on the first type of feature and the second type of feature (block 470).

In some implementations, platform 220 may access a pool of analysis models. For example, the pool of analysis models may refer to a set of models that may be used to perform a biosignal analysis task. In this case, platform 220 may select a particular analysis model, from among the pool of analysis models, in order to perform the selected biosignal analysis task.

Platform 220 may identify the waveform model based on the selected biosignal analysis task. That is, platform 220 may store, in a data structure, information that maps analysis models, biosignal analysis tasks, waveform models, and DSP models. In other words, platform 220 may identify the particular waveform model to be used to perform the biosignal analysis task, based on the selected biosignal analysis task, the waveform model, and/or the DSP model.

As further shown in FIG. 4, process 400 may include performing, using the analysis model, the biosignal analysis task based on the first type of feature and the second type of feature (block 480).

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method for performing a biosignal analysis task using a set of models, the method performed by at least one processor and comprising:
   receiving an input biosignal, the input biosignal including a biosignal related to a heartbeat pattern, the biosignal including multiple types from among an electrocardiogram (ECG) signal, an electroencephalogram (EEG) signal, an electromyogram (EMG) signal, a mechanomyogram (MMG) signal, an electrooculography (EOG) signal, a galvanic skin response (GSR) signal, and a magnetoencephalogram (MEG) signal;
   receiving information that identifies a plurality of types of the biosignal analysis task to be performed in association with the input biosignal, the plurality of types including determining a diagnosis of a heart-related condition associated with the input biosignal, clustering the input biosignal, classifying the input biosignal, and predicting a heart-related disease associated with the input biosignal;
   accessing a storage configured to store information of first mapping that maps waveform models, of a set of waveform models, and biosignal analysis tasks in association with each other and configured to store information of second mapping that maps digital signal processing (DSP) models, of a set of DSP models, and the biosignal analysis tasks in association with each other;
   selecting, by using a waveform feature extraction module, a waveform model, from the set of waveform models, based on the information that identifies a first type, among the identified plurality of types of the biosignal analysis task to be performed and the information of the first mapping, wherein the waveform model includes a combination of two or more from a recurrent neural network (RNN), a convolutional neural network (CNN), and a support vector machine (SVM);
   selecting, by using a DSP feature extraction module, a DSP model, from the set of DSP models, based on the information that identifies a second type, among the identified plurality of types of the biosignal analysis task to be performed and the information of the second mapping;
   simultaneously extracting, from the input biosignal, a first type of feature of the input biosignal by using the waveform model, selected by the waveform feature extraction module, and a second type of feature of the input biosignal by using the DSP model, selected by the DSP feature extraction module, wherein the first type of feature includes a waveform of the input biosignal, an amplitude of the input biosignal, and a frequency of the input biosignal, and wherein the DSP feature extraction module performs a signal processing algorithm including a fast Fourier transform, a wavelet transform, and a filter, to obtain the second type of feature;
   selecting an analysis model, from a set of analysis models, to perform the biosignal analysis task associated with the input biosignal, based on the first type of feature and the second type of feature, the selected analysis model being configured to receive the extracted first and second types of features and produce final outcomes including a classification result, an outlier alarms, and a predicted diagnosis based on the received extracted first and second types of features, wherein
   the storage is configured to store information that maps analysis models, biosignal analysis tasks, waveform models, and DSP models in association with each other, and the selecting the analysis model is performed by referring to the storage using the biosignal analysis task, the selected waveform model, and the selected DSP model,
   the set of analysis models includes a plurality of statistical process control algorithms for biosignal monitoring and alarming, a plurality of predictive models and classifier models for computer-aided diagnosis, and a plurality of statistical tools for general pathological status calculation, and
   the selected analysis model is configured to perform a multi-symptom diagnosis by using a dependency between symptoms, a feedback link being added from the diagnosed multi-symptom to feature extraction modules; and
   performing, using the analysis model, the identified plurality of types of the biosignal analysis task based on the first type of feature and the second type of feature extracted simultaneously by the waveform model and the DSP model to diagnose the heart-related condition associated with the input biosignal, cluster the input biosignal, classify the input biosignal, or predict the heart-related disease associated with the input biosignal, wherein the waveform feature extraction module and the DSP feature extraction module are based on machine learning, and parameters for the waveform feature extraction module and parameters for the DSP feature extraction module are separately trained and selected, to model a relationship between an input of a biosignal and an output of each of the plurality of types of the biosignal analysis task.

2. The method of claim 1, wherein the biosignal analysis task includes at least one of biosignal monitoring, biosignal alarming, and patient monitoring.

3. The method of claim 1, further comprising:
receiving another type of biosignal; and
performing the identified first or second type of the biosignal analysis task using the another type of biosignal.

4. A device for performing a biosignal analysis task using a set of models, comprising:
at least one memory configured to store program code; and
at least one processor configured to read the program code and operate as instructed by the program code, the program code including:
receiving code configured to cause the at least one processor to:
receive an input biosignal, the input biosignal including a biosignal related to a heartbeat pattern, the biosignal including multiple types from among an electrocardiogram (ECG) signal, an electroencephalogram (EEG) signal, an electromyogram (EMG) signal, a mechanomyogram (MMG) signal, an electrooculography (EOG) signal, a galvanic skin response (GSR) signal, and a magnetoencephalogram (MEG) signal, and
receive information that identifies a plurality of types of the biosignal analysis task to be performed in association with the input biosignal, the plurality of types including determining a diagnosis of a heart-related condition associated with the input biosignal, clustering the input biosignal, classifying the input biosignal, and predicting a heart-related disease associated with the input biosignal;
accessing code configured to cause the at least one processor to access a storage configured to store information of first mapping that maps waveform models, from a set of waveform models, and biosignal analysis tasks in association with each other and configured to store information of second mapping that maps digital signal processing (DSP) models, of a set of DSP models, and the biosignal analysis tasks in association with each other;
first selecting code configured to cause the at least one processor to:
select, by using a waveform feature extraction module, a waveform model, from the set of waveform models, based on the information that identifies a first type, among the identified plurality of types of the biosignal analysis task to be performed and the information of the first mapping, wherein the waveform model includes a combination of two or more from a recurrent neural network (RNN), a convolutional neural network (CNN), and a support vector machine (SVM), and
select, by using a DSP feature extraction module, a DSP model, from the set of DSP models, based on the information that identifies a second type, among the identified plurality of types of the biosignal analysis task to be performed and the information of the second mapping;
extracting code configured to cause the at least one processor to simultaneously extract, from the input biosignal, a first type of feature of the input biosignal and by using the waveform model, selected by the waveform feature extraction module, and a second type of feature of the input biosignal by using the DSP model, selected by the DSP feature extraction module, wherein the first type of feature includes a waveform of the input biosignal, an amplitude of the input biosignal, and a frequency of the input biosignal, and wherein the DSP feature extraction module performs a signal processing algorithm including a fast Fourier transform, a wavelet transform, and a filter, to obtain the second type of feature;
second selecting code configured to cause the at least one processor to select an analysis model, from a set of analysis models, to perform the identified plurality of types of the biosignal analysis task associated with the input biosignal, based on the first type of feature and the second type of feature, the selected analysis model being configured to receive the extracted first and second types of features and produce final outcomes including a classification result, an outlier alarms, and a predicted diagnosis based on the received extracted first and second types of features, wherein
the storage is configured to store information that maps analysis models, biosignal analysis tasks, waveform models, and DSP models in association with each other, and the selecting the analysis model is performed by referring to the storage using the biosignal analysis task, the selected waveform model, and the selected DSP model,
the set of analysis models includes a plurality of statistical process control algorithms for biosignal monitoring and alarming, a plurality of predictive models and classifier models for computer-aided diagnosis, and a plurality of statistical tools for general pathological status calculation, and
the selected analysis model is configured to perform a multi-symptom diagnosis by using a dependency between symptoms, a feedback link being added from the diagnosed multi-symptom to feature extraction modules; and
performing code configured to cause the at least one processor to perform, using the analysis model, the biosignal analysis task based on the first type of feature and the second type of feature extracted simultaneously by the waveform model and the DSP model to diagnose the heart-related condition associated with the input biosignal, cluster the input biosignal, classify the input biosignal, or predict the heart-related disease associated with the input biosignal,
wherein the waveform feature extraction module and the DSP feature extraction module are based on machine learning, and parameters for the waveform feature extraction module and parameters for the DSP feature extraction module are separately trained and selected, to model a relationship between an input of a biosignal and an output of each of the plurality of types of the biosignal analysis task.

5. The device of claim 4, wherein the biosignal analysis task includes at least one of biosignal monitoring, biosignal alarming, and patient monitoring.

6. The device of claim 4, wherein the receiving code is further configured to cause the at least one processor to receive another type of biosignal; and
  wherein the performing code is further configured to cause the at least one processor to perform the identified first or second type of the biosignal analysis task using the another type of biosignal.

7. A non-transitory computer-readable medium storing instructions, the instructions comprising: one or more instructions that, when executed by one or more processors of a device for performing a biosignal analysis task using a set of models, cause the one or more processors to:
  receive an input biosignal, the input biosignal including a biosignal related to a heartbeat pattern, the biosignal including multiple types from among an electrocardiogram (ECG) signal, an electroencephalogram (EEG) signal, an electromyogram (EMG) signal, a mechanomyogram (MMG) signal, an electrooculography (EOG) signal, a galvanic skin response (GSR) signal, and a magnetoencephalogram (MEG) signal;
  receive information that identifies a plurality of types of the biosignal analysis task to be performed in association with the input biosignal, the plurality of types including determining a diagnosis of a heart-related condition associated with the input biosignal, clustering the input biosignal, classifying the input biosignal, and predicting a heart-related disease associated with the input biosignal;
  access a storage configured to store information of first mapping that maps waveform models, from a set of waveform models, and biosignal analysis tasks in association with each other and configured to store information of second mapping that maps digital signal processing (DSP) models, of a set of DSP models, and the biosignal analysis tasks in association with each other;
  select, by using a waveform feature extraction module, a waveform model, from the set of waveform models, based on the information that identifies a first type, among the identified plurality of types of the biosignal analysis task to be performed and the information of the first mapping, wherein the waveform model includes a combination of two or more from a recurrent neural network (RNN), a convolutional neural network (CNN), and a support vector machine (SVM);
  select, by using a DSP feature extraction module, a DSP model, from the set of DSP models, based on the information that identifies a second type, among the identified plurality of types of the biosignal analysis task to be performed and the information of the second mapping;
  simultaneously extract, from the input biosignal, a first type of feature of the input biosignal by using the waveform model, selected by the waveform feature extraction module, and a second type of feature of the input biosignal by using the DSP model, selected by the DSP feature extraction module, wherein the first type of feature includes a waveform of the input biosignal, an amplitude of the input biosignal, and a frequency of the input biosignal, and wherein the DSP feature extraction module performs a signal processing algorithm including a fast Fourier transform, a wavelet transform, and a filter, to obtain the second type of feature;
  select an analysis model, from a set of analysis models, to perform the biosignal analysis task associated with the input biosignal, based on the first type of feature and the second type of feature, the selected analysis model being configured to receive the extracted first and second types of features and produce final outcomes including a classification result, an outlier alarms, and a predicted diagnosis based on the received extracted first and second types of features, wherein
    the storage is configured to store information that maps analysis models, biosignal analysis tasks, waveform models, and DSP models in association with each other, and selecting the analysis model is performed by referring to the storage using the biosignal analysis task, the selected waveform model, and the selected DSP model,
    the set of analysis models includes a plurality of statistical process control algorithms for biosignal monitoring and alarming, a plurality of predictive models and classifier models for computer-aided diagnosis, and a plurality of statistical tools for general pathological status calculation, and
    the selected analysis model is configured to perform a multi-symptom diagnosis by using a dependency between symptoms, a feedback link being added from the diagnosed multi-symptom to feature extraction modules; and
  perform, using the analysis model, the identified plurality of types of the biosignal analysis task based on the first type of feature and the second type of feature extracted simultaneously by the waveform model and the DSP model to diagnose the heart-related condition associated with the input biosignal, cluster the input biosignal, classify the input biosignal, or predict the heart-related disease associated with the input biosignal,
  wherein the waveform feature extraction module and the DSP feature extraction module are based on machine learning, and parameters for the waveform feature extraction module and parameters for the DSP feature extraction module are separately trained and selected, to model a relationship between an input of a biosignal and an output of each of the plurality of types of the biosignal analysis task.

8. The non-transitory computer-readable medium of claim 7, wherein the biosignal analysis task includes at least one of biosignal monitoring, biosignal alarming, and patient monitoring.

* * * * *